(12) United States Patent
Unkefer et al.

(10) Patent No.: US 8,551,917 B2
(45) Date of Patent: Oct. 8, 2013

(54) USE OF PROLINES FOR IMPROVING GROWTH AND/OR YIELD

(75) Inventors: Pat J. Unkefer, Los Alamos, NM (US); Rodolfo A. Martinez, Santa Fe, NM (US); Thomas J. Knight, Raymond, ME (US)

(73) Assignee: Los Alamos National Security, LLC, Los Alamos, NM (US)

( * ) Notice: Subject to any disclaimer, the term of this patent is extended or adjusted under 35 U.S.C. 154(b) by 921 days.

(21) Appl. No.: 11/269,417

(22) Filed: Nov. 7, 2005

(65) Prior Publication Data

US 2007/0105719 A1    May 10, 2007

(51) Int. Cl.
*A01N 43/36*   (2006.01)
*A61K 9/00*    (2006.01)

(52) U.S. Cl.
USPC .......................................... 504/138; 424/400

(58) Field of Classification Search
None
See application file for complete search history.

(56) References Cited

U.S. PATENT DOCUMENTS

| | | | |
|---|---|---|---|
| 3,899,585 | A | 8/1975 | Misato et al. |
| 5,922,649 | A | 7/1999 | Pehu et al. |
| 6,083,876 | A | 7/2000 | Jokinen et al. |
| 6,329,571 | B1 | 12/2001 | Hiei |
| 6,767,865 | B2 | 7/2004 | Den Tandt et al. |
| 6,831,040 | B1 | 12/2004 | Unkefer et al. |
| 7,001,869 | B2 | 2/2006 | Johnson |
| 2003/0032149 | A1 | 2/2003 | Lalonde |
| 2004/0063582 | A1 | 4/2004 | Johnson |
| 2004/0209777 | A1 | 10/2004 | Gemma et al. |
| 2005/0232868 | A1* | 10/2005 | Rennie et al. .................. 424/45 |
| 2006/0090219 | A1 | 4/2006 | Kisaka |
| 2007/0105719 | A1 | 5/2007 | Unkefer |

FOREIGN PATENT DOCUMENTS

| | | | |
|---|---|---|---|
| EP | 1095565 A1 | | 5/2001 |
| EP | 1647181 | | 4/2006 |
| JP | 2005-512963 | | 5/2005 |
| RU | 2277323 | | 6/2006 |
| RU | 2006104849 | | 6/2006 |
| WO | WO 01/54500 | * | 8/2001 |
| WO | WO 03/026422 | | 4/2003 |
| WO | WO 03/026429 | * | 4/2003 |
| WO | WO 2007/056409 | | 5/2007 |

OTHER PUBLICATIONS

Walkey et al. (J. gen. Virol., 5, 237-241, 1969), The inactivation of virus in cultured . . . .*
Johnson, "Seed Treatment and Method of Treating Seed," US 2004/0063582 A1, Apr. 1, 2004.
Nanjo, "Bilogical Functions of Proline in Morphogenesis and Osmotolerance Revealed in Antisense Transgenic *Arabidopsis thaliana*," The Plant Journal, 1999, 18(2), 185-193.
Nanjo, T. et al., "Biological functions of proline in morphogenesis and osmotolerance revealed in antisense transgenic *Arapidopsis thaliana*." The Plant Journal, vol. 18, No. 2 (Feb. 1999) pp. 185-193.
Brochure: Take Off™, Verdesian Life Sciences, LLC, 12 pages, Undated.

* cited by examiner

*Primary Examiner* — David J Blanchard
*Assistant Examiner* — Tigabu Kassa
(74) *Attorney, Agent, or Firm* — Woodcock Washburn, LLP

(57) ABSTRACT

The present invention describes a composition including a mixture of L- and D-pyroglutamate stereoisomers in a ratio of L to D of from about 80:20 to about 97:3, and, a carrier medium for application of the L- and D-pyroglutamate stereoisomers to a target plant. The composition can also be used as a germination medium and may be incorporated into a seed coat for assisting in germination. The present invention further describes a method of increasing the agronomic performance of a target plant by treating a target plant with a composition including a mixture of L- and D-pyroglutamate stereoisomers in a ratio of L to D of from about 80:20 to about 97:3 and a carrier medium for said L- and D-pyroglutamate stereoisomers.

18 Claims, No Drawings

USE OF PROLINES FOR IMPROVING GROWTH AND/OR YIELD

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to selected proline-containing compositions and the use of such proline-containing compositions for improving plant growth, for improving seed germination, for protecting plants against selected stress conditions and the like.

BACKGROUND OF THE INVENTION

Many agricultural activities are highly time sensitive, with costs and returns being dependent upon a rapid turnover of crops or upon being first to market. Therefore, rapid plant growth is an economically important goal for many agricultural businesses that grow high-value crops such as vegetables, berries, and bananas, as well as for the greenhouse and nursery industry. The importance of improved crop production technologies has magnified as observations have indicated that yields for many well-developed crops have tended to plateau in recent years. The goal of rapid plant growth has been addressed in numerous studies of plant regulatory mechanisms, which remain incompletely understood. In particular, a complete understanding has not been attained for the plant regulatory mechanisms that coordinate carbon and nitrogen metabolism, which must have a major impact on plant growth and development.

Similarly to the desire for rapid plant growth, other plant factors are important to the agricultural industry including factors such as: length of time until seed germination, uniformity of germination, i.e., nearly simultaneously germination, yield, and the ratio of total seed germination.

U.S. Pat. No. 5,922,649 by Pehu et al. illustrates application of a composition, specifically a glycine betaine composition, to improve the yield of plants.

U.S. Pat. No. 6,831,040 by Unkefer et al. illustrates application of prolines such as 2-hydroxy-5-oxoproline, 5-oxoproline (2-pyrrolidone-5-carboxylic acid) and mixtures thereof to plants can promote growth. Maintaining an effective concentration of either or both 2-oxoglutaramate and pyroglutamate in a plant is highly desirable. Elevation of the concentration of the 2-oxoglutaramate can result in improved performance, quality traits and other benefits. Treating plants with 2-oxoglutaramate or pyroglutamate can provide these benefits. To date, methods aimed at maximizing the benefits of pyroglutamate have generally required regular, frequent treatments to maintain the desired levels of the compound.

The present inventors made an extensive investigation of compositions including L and D isomers of pyroglutamate in various ratios and the efficacy of such compositions in promoting seed germination, plant growth and yield. The inventors have found preferred or optimal compositions for promoting such plant growth and yield.

SUMMARY OF THE INVENTION

In accordance with the purposes of the present invention, as embodied and broadly described herein, the present invention includes a composition including a mixture of L- and D-pyroglutamate stereoisomers in a ratio of L to D of from about 80:20 to about 97:3; and, a carrier medium for application of said L- and D-pyroglutamate stereoisomers to a target plant.

The present invention also includes a method of increasing the growth or yield of a target plant by treating a target plant with a composition including a mixture of L- and D-pyroglutamate stereoisomers in a ratio of L to D of from about 80:20 to about 97:3 and a carrier medium for said L- and D-pyroglutamate stereoisomers.

The present invention also includes a method of treating seeds prior to planting comprising wetting the seeds directly with a solution of a composition including a mixture of L- and D-pyroglutamate stereoisomers in a ratio of L to D of from about 80:20 to about 97:3.

The present invention also includes the improvement to a seed coating composition of adding a mixture of L- and D-pyroglutamate stereoisomers in a ratio of L to D of from about 80:20 to about 97:3 as one component of the seed coating composition.

DETAILED DESCRIPTION

Pyroglutamate exists in two forms, the D and L stereoisomers. Each of these isomers is active at generating the desired benefits in plants. The commercially available pyroglutamate, synthesized by a bacterial fermentation process, has a stereochemistry ratio of approximately 60:40 of the L isomer to the D isomer.

The present invention is concerned with compositions including L and D isomers of pyroglutamate in various ratios and the efficacy of such compositions in promoting seed germination, plant growth and yield, and resistance to stresses. Preferred or optimal compositions for promoting such plant growth and yield have now been found. In particular, the present invention is concerned with compositions including mixtures of L- and D-pyroglutamate stereoisomers having a L to D stereoisomer ratio of from about 80:20 to about 97:3. Such compositions are also useful as seed germination mediums and can be employed in a seed coat for enhancing seed germination. The present invention is further concerned with efficacy or effectiveness of pyroglutamate compositions having selected ratio of L to D stereoisomers for application in a carrier to targeted plants for promoting plant growth and yield.

The composition of the present invention has properties conducive for increasing plant productivity. For example, by careful control of the L:D stereoisomer ratio at from about 80:20 to about 97:3, an unexpected greater stimulation of plant growth occurs than is possible using either stereoisomer alone. The compositions can also be effective at protecting plants from stresses such as those received by the intentional or inadvertent application of a herbicide. Additionally, these compositions can be applied as a germination medium or used in a seed coat composition to provide enhanced germination of seeds.

In one embodiment of the present invention, the compositions including a mixture of L- and D-pyroglutamate stereoisomers with a L to D stereoisomer ratio of from about 80:20 to about 97:3 may be combined with a carrier medium as known in the art. For example, the compositions may be in water, including distilled and tap water, in a fertilizer solution, or in a herbicide solution. The herbicide may be an agricultural chemical such as 2,4-D (2,4-dichlorophenoxy acetic acid) and the like. One skilled in the art would be familiar with the various fertilizer and herbicide solutions that may be employed. However, the pyroglutamate compositions of the present invention can most simply be combined with water.

In another embodiment of the present invention, the compositions including a mixture of L- and D-pyroglutamate stereoisomers with a L to D stereoisomer ratio of from about 80:20 to about 97:3 may be combined into a seed coating composition, such seed coating compositions well known in the art. Those skilled in the art are familiar with the various seed coat compositions that may be employed.

The pyroglutamate compositions of the present invention can simply be added as one component of conventional seed coatings. Such conventional seed coatings are often polymeric or a clay and can be used to protect the seed from abrasion during the storage and planting stages, from unfavorable environmental conditions after planting, to protect the seed from insects, fungus and the like through the use of additives such as fungicides and insecticides, or to promote potential germination at a more desirable time as may relate to temperature, moisture and the like. Seed coatings are also used t provide compounds that improve overallplant or seed performance. For example, a polymeric coating may be designed to degrade at pre-selected temperatures or moisture levels whereby seeds can be planted earlier than the optimal germination time and the seed coating will delay the germination until environmental conditions are suitable.

The composition may also include a carrier. By the term "carrier" is meant an organic or inorganic natural or synthetic material with which the active material, i.e., the mixture of L- and D-pyroglutamate stereoisomers, can be associated to facilitate its application to a plant, to seeds, or to soil proximate to seeds and/or plants. The carrier can also facilitate transportation or handling of seeds and/or plants. The support can be a solid (e.g., clays, natural or synthetic silicates, resins and waxes) or fluid (e.g., water, alcohols, ketones, petroleum fractions, chlorinated hydrocarbons and liquified gases).

The pyroglutamate compositions of the present invention may also include one or more surfactants which may assist in the penetration of active components into plants. Such surfactants include anionic, cationic, non-ionic and zwitterionic surfactant. Anionic surfactants include alkyl aryl ethoxylates, fatty acid ethoxylates, vegetable seed oil ethoxylates, sorbitan fatty acid ester ethoxylates, or other alkoxylates. Suitable surfactants can include sodium docecyl sulfate and the compound, $C_9H_{19}$-(phenylene)-$(OCH_2 CH_2)_9OH$ also known as Nonoxynol-9™ or NP-9™.

The pyroglutamate compositions of the present invention may also include one or more wetting agents such as glycerol and the like.

The pyroglutamamte compositions of the present invention may be advantageously applied to plants by any one of a number of means. For example, the compositions may be applied directly to the roots of the plants, by spraying on the foliage of the plants, by applying to the soil around the plants and the like. Preferably, the compositions may be applied by spraying on the foliage of the plants.

The methods and pyroglutamate compositions of the present invention may be used with recreational or decorative plants or with recreational or decorative crops but is particularly useful for treating commercial crops. Examples of plants and crops that may be treated in the present invention include: monocotyledons (monocots), such as sorghum, rice, wheat, corn, barley, oats, and turf, i.e., grasses; dicotyledons (dicots), such as roses and fruit trees including apples, cherries, and peaches; vines including grapes and the like, vegetable crucifers (such as broccoli, cauliflower, brussel sprouts, kale, collard, radishes and cabbage); solanaceae (potatoes, tomatoes, and peppers including green peppers, chili peppers and the like); and, legumes such as soybeans, bush beans and the like.

The pyroglutamate compositions and process of the present invention considerably improves the growth and yield of plants, for example the amount and quantity of the yield. The pyroglutamate compositions and process of the present invention can be economically advantageous and the increase in the yield can be economically profitable and significant. For example the amount of oat yield has been demonstrated to increase with a suitable application of the described mixtures of L- and D-pyroglutamate stereoisomers.

The present invention is more particularly described in the following examples, which are intended as illustrative only, since numerous modifications and variations will be apparent to those skilled in the art.

EXAMPLE 1

Individual batches of oat seedlings were treated one time with the series of pyroglutamate isomer mixtures shown in Table 1. Leaves were counted to track plant growth rate for the next 28 days.

TABLE 1

| | Series composition | |
|---|---|---|
| Series Number | % of L isomer | % of D isomer |
| #1 | 0 | 100 |
| #2 | 60 | 40 |
| #3 | 70 | 30 |
| #4 | 80 | 20 |
| #5 | 90 | 10 |
| #6 | 95 | 5 |
| #7 | 96 | 4 |
| #8 | 97 | 3 |
| #9 | 98 | 2 |
| #10 | 99 | 1 |
| #11 | 99.6 | 0.4 |
| #12 | 100 | 0 |
| #13 (blank) | 0 | 0 |

The best plant growth rate, based on days since treatment versus total leaves, was found with the following ratios of L/D isomer: 80/20; 90/10; and, 95/5. Each of these ratios outperformed the standard commercially available material having a L/D ratio of 60/40 (series #2).

EXAMPLE 2

The oats from example 1 were also monitored for their number of tillers with flag leaves emerged at day 28 post-treatment. This parameter relates to potential for grain yield. Table 2 contains the resultant tillers with flag leaves at 28 days for the same series of isomer mixtures.

TABLE 2

| | Series number | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Tillers with flag leaves | 20 | 24 | 17 | 34 | 33 | 37 | 29 | 31 | 23 | 22 | 26 | 24 | 19 |

The best performance was found with the ratios of L/D isomer from 80/20 to 97/3. Each of these ratios clearly outperformed the standard commercially available material having a L/D ratio of 60/40 (series #2).

EXAMPLE 3

Oat seedlings were treated with the series of pyroglutamate isomer mixtures shown in Table 2. Leaves were counted to track plant growth rate for the next 24 days.

TABLE 2

| Series Number | Series composition | |
|---|---|---|
| | % of L isomer | % of D isomer |
| #1 | 77.5 | 22.5 |
| #2 | 80 | 20 |
| #3 | 85 | 15 |
| #4 | 90 | 10 |
| #5 | 92.5 | 7.5 |
| #6 (blank) | 0 | 0 |

The best plant growth rate, based on days since treatment versus total leaves as a percentage of day 1 leaves, was found with the ratios of L/D isomer of 80/20, 90/10 and 92.5/7.5.

An examination of the results of examples 1 through 3 demonstrates that improved plant performance was achieved using ratios of L/D isomers of pyroglutamate between about 80/20 and 97/3.

EXAMPLE 4

Three year old tomato seeds (Heinz #9665) were treated with aerated water (control) and with various solutions of the pyroglutamate composition (isomer ratio 85:15 of L:D). The seeds were soaked (imbibed) for four hours in the respective liquid and then spread out onto germination paper in standard phytotrays (at 25° C. in the dark).

An initial pyroglutamate composition (with the 85:15 isomer ratio) was prepared at a concentration of 13.7 grams per liter at a pH of between about 6.0 and 6.5. This composition is referred to as standard solution. In addition to the control, seeds were treated in the following final concentrations of pyroglutamate composition: standard solution (I); 1/10 standard solution (II); 1/100 standard solution (III); and, 1/1000 standard solution (IV).

At day 2, a pronounced stimulation of germination was observed in seeds treated with the 1/100 standard solution (III) and the 1/1000 standard solution (IV) in comparison to zero germination for the control and for the standard solution (I) and the 1/10 standard solution (II).

Examination of the various seeds treated by the control solution, the standard solution (I) or the 1/10 standard solution (II), revealed that zero percent of the seeds demonstrated any swelling of embryo or emergence of shoot radicles. In comparison, seeds treated with either the 1/100 standard solution (III) or the 1/1000 standard solution (IV) showed that about 25 percent of the seeds had swollen embryo or emerging shoot radicles.

At day 6 after initial treatment, the following germination levels were observed: for the control solution, 62 percent germination; for the standard solution (I), zero percent germination; for the 1/10 standard solution (II), 64 percent germination; for the 1/100 standard solution (III), 86 percent germination; and for the 1/1000 standard solution (IV), 88 percent germination.

From these results, positive results on: time of germination of the seeds, i.e., speed of germination of the seeds; percentage of germination; and, developmental rate of the seedlings are indicated.

EXAMPLE 5

Commercial field grown wheat was sprayed one time with the pyroglutamate composition (isomer ratio 85:15 of L:D) at the flag leaf stage using the same treatment solution as described in our other plant treatments. Grain was harvested at maturity; the treated plots yielded 0.65 T/hectare more (7% increase) grain (seed) than the untreated plots.

EXAMPLE 6

Commercial field grown table grapes were at sprayed twice the first time at 6-12" of new vine growth and the second spraying 2 months later. The pyroglutamate composition (isomer ratio 85:15 of L:D) was applied at a rate of 25 gm per acre. The treated grapes produced 13.5% greater yield of harvestable grapes (1045 standard boxes) than the untreated plots (921 standard boxes).

EXAMPLE 7

A test was conducted to measure mitigation by pyroglutamate of 2,4-D-induced stress in a monocotyledonous crop plant, oats.

Growing oat plants were treated with a mixture of pyroglutamate (isomer ratio 85:15 of L:D) and 2,4-D and their growth monitored. Oat seedlings, growing vigorously in a greenhouse, were treated with a mixture of 2,4-D and pyroglutamate (13.5 g/L). The 2,4-D was included in the mixture at 1/4 of the recommended field strength; a surfactant/wetting agent (Gly Surf P) was also used. The treatment solution was applied with a backpack R&D sprayer using 2 passes over the plants to assure that all plants received treatment solution. It was estimated that this simulated a 1/2 strength field dose. These plants were compared with plants treated with the herbicide and surfactant/wetting agent as well as with controls treated only with the surfactant/wetting agent (controls).

It was found that plants treated with 1/4 field strength 2,4-D and pyroglutamate were larger than those treated with only 2,4-D. The average plant fresh weight of the control plants was 10.4 g, while the average plant fresh weight of the plants treated with the 1/4 field strength 2,4-D was 2.29 g and the average plant fresh weight of the plants treated with the 1/4 field strength 2,4-D with the pyroglutamate was 7.11 g. Thus, the incorporation of pyroglutamate with the herbicide clearly lessened the negative impact of the herbicide. The possibilities of this include both: (a) using treatment of plants with the pyroglutamate where herbicide might be unintentionally oversprayed; and, (b) direct use of a combination of both an appropriate herbicide and pyroglutamate (of a preselected isomer ratio such as 85:15 of L:D).

EXAMPLE 8

A test was conducted to demonstrate that a formulation of a herbicide (2,4-D) with pyroglutamate (isomer ratio 85:15 of L:D) added did not reduce the efficacy of the herbicidal effect on dicotyledenous plants.

Two dicotyledenous plants, white clover and morning glory were treated with the manufacturer's recommended field strength application and the killing rate was measured. Growing morning glory and clover plants (25 each treatment) treated with either 2,4-D alone or a mixture of 2,4-D and pyroglutamate were killed with the same efficacy, 100%.

Although the present invention has been described with reference to specific details, it is not intended that such details should be regarded as limitations upon the scope of the invention, except as and to the extent that they are included in the accompanying claims.

What is claimed is:

1. A composition comprising a mixture of L- and D-pyroglutamate stereoisomers in a ratio of L to D of from about 80:20 to 97:3; and, a carrier medium for application of said L- and D-pyroglutamate stereoisomers to a target plant.

2. The composition of claim 1 wherein said ratio of L to D stereoisomers is from about 80:20 to about 95:5.

3. The composition of claim 1 wherein said carrier medium is an aqueous solution including a surfactant and a wetting agent.

4. The composition of claim 3 wherein said composition further includes a herbicide.

5. The composition of claim 4 wherein said herbicide is 2,4-dichlorophenoxy acetic acid.

6. A method of increasing the agronomic performance of a target plant comprising: treating a target plant with a composition including a mixture of L- and D-pyroglutamate stereoisomers in a ratio of L to D of from about 80:20 to 97:3 and a carrier medium for said L- and D-pyroglutamate stereoisomers.

7. The method of claim 6 wherein said ratio of L to D stereoisomers is from about 80:20 to about 95:5.

8. The method of claim 6 wherein said carrier medium is an aqueous solution including a surfactant and a wetting agent.

9. The method of claim 6 wherein said target plant is selected from the group consisting of monocots, dicots, crucifers, solanaceae and legumes.

10. The method of claim 6 wherein said treating is by application to foliage of a target plant or by application to roots of a target plant.

11. The method of claim 9 wherein said composition further includes a herbicide.

12. The method of claim 11 wherein said herbicide is 2,4-dichlorophenoxy acetic acid.

13. The method of claim 6 wherein said agronomic performance is selected from the group consisting of plant growth, flowering potential, plant yield and resistance to stress from a herbicide.

14. The method claim 10 wherein said treating is by application to foliage of a target plant.

15. The method of claim 10 wherein said treating is by application to roots of a target plant.

16. A method of treating seeds prior to planting comprising wetting the seeds directly with a solution of a composition including a mixture of L- and D-pyroglutamate stereoisomers in a ratio of L to D of from about 80:20 to 97:3.

17. The method of claim 16 wherein said seeds are selected from the group consisting of rice and peppers.

18. In a seed coating composition, the improvement comprising adding a mixture of L- and D-pyroglutamate stereoisomers in a ratio of L to D of from about 80:20 to 97:3 as one component of said seed coating composition.

* * * * *